United States Patent
Kamen et al.

(10) Patent No.: US 11,964,131 B2
(45) Date of Patent: Apr. 23, 2024

(54) SYRINGE SHIELD, SYRINGE SHIPPING AND ADMINISTRATION SYSTEM, AND COMPONENTS THEREFOR

(71) Applicant: Robert Kamen, Toronto (CA)

(72) Inventors: Robert Kamen, Toronto (CA); Mico Segrt, Hamilton (CA); Rasho Petrovic, Stoney Creek (CA)

(73) Assignee: Robert Kamen, Toronto (CA)

( * ) Notice: Subject to any disclaimer, the term of this patent is extended or adjusted under 35 U.S.C. 154(b) by 524 days.

(21) Appl. No.: 17/278,598

(22) PCT Filed: Sep. 26, 2019

(86) PCT No.: PCT/CA2019/051381
§ 371 (c)(1),
(2) Date: Mar. 22, 2021

(87) PCT Pub. No.: WO2020/061705
PCT Pub. Date: Apr. 2, 2020

(65) Prior Publication Data
US 2021/0353859 A1  Nov. 18, 2021

Related U.S. Application Data

(60) Provisional application No. 62/852,381, filed on May 24, 2019, provisional application No. 62/801,993, filed on Feb. 6, 2019, provisional application No. 62/736,885, filed on Sep. 26, 2018.

(51) Int. Cl.
*A61M 5/178* (2006.01)
*A61M 5/00* (2006.01)

(52) U.S. Cl.
CPC .......... *A61M 5/1785* (2013.01); *A61M 5/002* (2013.01); *A61M 5/007* (2013.01)

(58) Field of Classification Search
CPC ..... A61M 5/1785; A61M 5/002; A61M 5/007
See application file for complete search history.

(56) References Cited

U.S. PATENT DOCUMENTS

| | | |
|---|---|---|
| 5,519,931 A | 5/1996 | Reich |
| 6,828,577 B2 | 12/2004 | Zens |
| 7,307,265 B2 | 12/2007 | Polsinelli et al. |
| 7,312,465 B2 | 12/2007 | Schaber |
| 7,473,918 B2 | 1/2009 | Yanke et al. |
| 2005/0234424 A1 | 10/2005 | Besing et al. |
| 2008/0086092 A1 | 4/2008 | Loe |

*Primary Examiner* — Nicole M Ippolito
*Assistant Examiner* — Hanway Chang
(74) *Attorney, Agent, or Firm* — Dickinson Wright LLP; Matthew D. Powell (57) ABSTRACT

A shield for a syringe containing biohazardous material includes an elongate body comprising a compartment extending longitudinally therethrough from a body cold end to a body hot end, the compartment dimensioned to receive a syringe barrel; a cold end cover dimensioned to receive and enclose a syringe plunger extending beyond the body cold end, the cold end cover attachable at the body cold end for enclosing the compartment and the syringe plunger at the body cold end thereby to shieldingly contain the biohazardous material in the syringe at the body cold end; and a hot end cover attachable at the body hot end for at least enclosing the compartment at the body hot end thereby to shieldingly contain the biohazardous material in the syringe at the body hot end.

18 Claims, 8 Drawing Sheets

Certificate of Compliance for Radioactive Materials Package
D.O.T. Specification 7A, Type A

1. Package Identification: Common name: Single of Multiple Dose Shipping System Model T717-S (with 11 Biodex Pigs), Syringe w/needle or without needle – Ground or Air Shipment.

2. PREAMBLE
   2a. This certificate is issued to satisfy section 178.350 including sections 171.2, 173.403, 173.410, 173.411, 173.412, 173.415, 173.415 (a), 173.431, 173.465, 173.466 and 178.608 of the Department of Transportation Hazardous Materials Regulations (49 CFR).

2b. The packaging and contents described in item 4 below meet the safety standards and were tested according to strict recommendations for general performance testing from:

IATA Dangerous Good Regulations, 56th Edition, Section 5.0.4.3, 10.5, and 10.6.1 thru 10.6.3.5 . 49 CFR as listed in item 2a above.

2c. This certificate does not release the consignor from complying with any requirements from the U.S Department of Transportation or any other applied regulatory agencies, including the governments of any countries through which the package will be transported.

3. Descriptions of Packaging and Authorized contents, other Conditions, And References:

*PIGs :11 pieces of Biodex PIG Model 001-280, 001-281, 001-282*
   Manufacturer: Biodex
   Material: Lead and Polymer
   Dimensions: 1.94" (Dia) x 8.52 " (H)

Figure 24a (Biodex is trademark of Biodex Medical Systems)
Syringe: 1- Becton, Dickinson : 3,5,8,10cc. plastic sytines
        2- Duopross 3,5,10cc Retractable Safety Syringes
Needles: 1- Becton, Dickinson Company
        2- Duopross
Shipping Bag: Model T-717-S Material: Nylon, PVC and Polymer laminate, Size: 11 in (W) x 6 in(Deep) x 9.8 in (H).
Foam: Material: Polymer, A)Top foam T712-1 : size 10.4 in X 9.25in X 1.5 in. B) Bottom foam T714-1: size 10.8 inX 9.5in X 2.15 in.

Authorized Contents:
Normal form Radioactive Material in Type A quantities.

Specification and Restrictions:
Ground or Air transportation.

4. This certificate is issued on basis of the test results, safety analysis reports of the package design.

5. Test Data File Name: Single and Multiple Dose Shipping system

6. CERTIFICATE
   This document is to certify that to the best of our knowledge all methods, packaging ,design and materials for building this package comply with the standard described in items 2a,2b,2c, herein. Any deviation from these conditions must be approved prior to use.

Approved:

Liu Li Hua
Manufacturer General Manager
and Senior Engineer.

Yao Su Sheng
Manufacturer Vice General Manager
and Senior Engineer.

Date: Dct 9, 2015

Zhang Yong Ping
Manufacture Manager and Senior Engineer.

Figure 24b

SYRINGE SHIELD, SYRINGE SHIPPING AND ADMINISTRATION SYSTEM, AND COMPONENTS THEREFOR

CROSS-REFERENCE TO RELATED APPLICATIONS

This application claims priority to U.S. Provisional Patent Application Ser. No. 62/736,885 entitled "SHIPPING SYSTEM FOR RADIOPHARMACEUTICAL UNIT DOSES" filed on Sep. 26, 2018, U.S. Provisional Patent Application Ser. No. 62/801,993 entitled "SHIPPING SYSTEM FOR PHARMACEUTICAL UNIT DOSES, AND ADAPTER THEREFOR" filed on Feb. 6, 2019, and U.S. Provisional Patent Application Ser. No. 62/852,381 entitled "LOCKING INSERT FOR RADIOPHARMACEUTICAL UNIT DOSE SHIPPING SYSTEM" filed on May 24, 2019, the contents of each of which is incorporated herein by reference.

FIELD OF THE INVENTION

This invention relates to hazardous materials, for example radiopharmaceuticals. In particular this invention relates to a syringe shield, a syringe shipping and administration system for storing, transporting and dispensing of biohazardous products and substances in liquid form, for example radiopharmaceuticals, and components therefor.

BACKGROUND OF THE INVENTION

There is a demand for shipping system that shields radiation and that enables transport of therapies containing certain radioactive isotopes, including, but not limited to, up to 1 Ci for I-131, up to 16.5 mCi for Ga-68, and up to 12 mCi for Cu-64. These compounds have been approved for, inter alia, diagnosis, localization, and treatment of different cancers.

Biohazardous materials and substances, for example radioactive materials or biological substances such as pathogens, can be dangerous and their transportation and handling are subject to strict controls.

For example, radioactive pharmaceutical products, commonly known as "radiopharmaceuticals," are prepared for patient injection, ingestion or other forms of administration in specially equipped and controlled facilities. Radiopharmaceuticals are well known for use as markers in nuclear medicine diagnostic procedures, and to treat certain diseases.

Unless properly shielded, such products become a radiation hazard for individuals handling them. For example, radioiodine pills or capsules that can be used for treating certain pathologies such as thyroid diseases or in conjunction with a diagnostic procedure to diagnose certain types of illnesses, are stored before use in a container typically made of plastic, for example a polyethylene pill bottle. In the case of a liquid radiopharmaceutical the container is typically a glass vial. Neither of these containers have any radioactivity-shielding properties. Therefore, the storage, transportation and dispensing of radiopharmaceuticals is carefully controlled by rules designed to regulate the handling of such materials in a manner that reduces the radiation hazard.

Each metered (for example assayed or calibrated) dose of the radiopharmaceutical product, for example in the case of a treatment for thyroid issues a radioiodine pill, or in the case of isotopes used in Nuclear Medicine (SPECT) and positron emission tomography (PET) diagnostic procedures a liquid, is placed by the manufacturer into the container to be shipped to a qualified facility for administration to a particular patient or patient category. At the radiopharmacy stock vials of different radiopharmaceuticals are dispensed as unit doses. This represents the first opportunity for hazardous exposure to the radioactive contents, and accordingly is done at the manufacturer in a shielded booth or other enclosure, or under other radioactivity-shielded conditions.

The container containing the radiopharmaceutical must then be shipped to the destination hospital or clinic for administration to the patient. To do this safely, the container is dropped into a radioactivity-shielding container commonly known as a "pig" for interim storage and delivery to the destination.

A conventional pig comprises a two-part vessel which is either formed from a radioactivity-shielding material, for example lead or tungsten, or has an exterior shell encasing a radiopharmaceutical container compartment that is lined with a radioactivity-shielding material such as lead or tungsten. A non-limiting example is described and illustrated in U.S. Pat. No. 6,586,758 issued Jul. 1, 2003 to Martin, which is incorporated herein by reference in its entirety.

When the pig is assembled, the radiopharmaceutical container compartment is sealed in order to contain the radiation and thus minimize human exposure to the radioactive contents of the radiopharmaceutical compartment. The compartment is sized to accommodate the radiopharmaceutical product, in the ingestible radioiodine example a pill or dissolving capsule, or in the case of a liquid of radiopharmaceutical a vial, syringe, ampule or other glass container. In each case the radiopharmaceutical compartment would be dimensioned accordingly.

Once the radiopharmaceutical container has been placed into the radiopharmaceutical compartment and the pig assembled, the pig is ready to be shipped to the patient's location. Because this part of the delivery process occurs entirely within the confines of the manufacturing plant, which is specifically designed and staffed so as to meet all regulatory guidelines and procedures, there is less chance of human exposure to the radioactive radiopharmaceutical product up to the point that the pill, capsule, vial, syringe or the like is sealed in the radiopharmaceutical container compartment of the pig. As is well known, the pig is designed to provide optimal shielding so as to reduce exposure during shipping. The transportation phase is a second opportunity for exposure to the radioactive contents of the radiopharmaceutical container, posing an occupational exposure opportunity for the driver/courier.

At the destination staff trained in handling radioactive substances, for example a nuclear medicine technologist or technician, opens the pig and then removes the closure from the radiopharmaceutical container to vent the container bottle. This is the third opportunity for exposure to the radioactive contents of the radiopharmaceutical container, in the presence of hospital or clinic staff. The technologist must transfer the radiopharmaceutical to a Dose Calibrator to assay (measure) the activity of the radiopharmaceutical, which must be within 10% of prescribed activity. After recording the assay, the technologist must retrieve the container containing the radiopharmaceutical and return the radiopharmaceutical container to the pig's radiopharmaceutical container compartment, which is the third opportunity for exposure to radioactivity. The technologist then applies the lid to the pig for delivery to the patient.

The pig is opened in the patient's presence in order to gain access to the radiopharmaceutical container and remove the container closure for administration of the radiopharmaceutical product to the patient, providing a fourth opportunity for exposure to the radioactive contents of the radiopharmaceutical container. In this step exposure of radioactivity to the ambient environment is unavoidable in order to access the radiopharmaceutical product for administration to the patient, so great care must be taken to handle the unshielded radiopharmaceutical product using proper safety equipment and procedures.

However, the assaying process, and the venting of the container in the case of certain volatile radioactive substances which produce radioactive iodine vapours such as 131 Iodine capsules, can present unnecessary points of risk of exposure to the technologist and other staff. Although the types of destination facilities to which these products are shipped are equipped to properly handle radiopharmaceutical products and the staff at such facilities are well trained in safety policies and procedures, this step can increase the risk of human exposure to the radioactive contents of the radiopharmaceutical product.

SUMMARY OF THE INVENTION

In accordance with an aspect of the invention, there is provided a shield for a syringe containing biohazardous material, the shield comprising an elongate body comprising a compartment extending longitudinally therethrough from a body cold end to a body hot end, the compartment dimensioned to receive a syringe barrel; a cold end cover dimensioned to receive and enclose a syringe plunger extending beyond the body cold end, the cold end cover attachable at the body cold end for enclosing the compartment and the syringe plunger at the body cold end thereby to shieldingly contain the biohazardous material in the syringe at the body cold end; and a hot end cover attachable at the body hot end for at least enclosing the compartment at the body hot end thereby to shieldingly contain the biohazardous material in the syringe at the body hot end.

In an embodiment, the elongate body is cylindrical.

In an embodiment, the shield comprises a first collar comprising an inner portion attached to the body cold end and an outer portion attachable to the cold end cover.

In an embodiment, the outer portion of the first collar comprises outwardly-projecting cams and the cold end cover comprises inwardly-projecting cams complementary to and engageable with the outwardly-projecting cams of the outer portion of the first collar thereby to enable bayonet attachment of the cold end cover at the body cold end.

In an embodiment, the shield further comprises a first gasket associated with the outer portion of the first collar and compressible between the cold end cover and the outer portion of the first collar during bayonet attachment thereby to inhibit unintentional detachment of the cold end cover from the outer portion.

In an embodiment, the shield comprises a second collar comprising an inner portion attached to the body hot end and an outer portion attachable to the hot end cover.

In an embodiment, the outer portion of the second collar comprises outwardly-projecting cams and the hot end cover comprises inwardly-projecting cams complementary to and engageable with the outwardly-projecting cams of the outer portion of the second collar thereby to enable bayonet attachment of the hot end cover at the body hot end.

In an embodiment, the shield further comprises a second gasket associated with the outer portion of the second collar and compressible between the hot end cover and the outer portion of the second collar during bayonet attachment thereby to inhibit unintentional detachment of the hot end cover from the outer portion.

In an embodiment, the shield further comprises a shielding sleeve lining an interior of the cold end cover to be intermediate the cold end cover and the syringe plunger; and a shielding puck at a distal end of the cold end cover to be intermediate the cold end cover and the syringe plunger.

In an embodiment, the cold end cover comprises a removable lid at the distal end of the cold end cover, the lid dimensioned to receive the shielding puck.

In an embodiment, the shield further comprises a shielding puck at a distal end of the hot end cover to be intermediate the hot end cover and a syringe tip.

In an embodiment, the shielding puck at the distal end of the hot end cover comprises an inlet dimensioned to at least partly receive the syringe tip while the hot end cover is attached at the body hot end.

In an embodiment, the shield further comprises a locking ring associated with the body cold end, the locking ring dimensioned to receive and engage a syringe hilt to enable selective inhibition of one or both of: longitudinal and rotational movement of the syringe with respect to the body.

In an embodiment, the locking ring of the shield comprises a ring body having an outer face and an inner face, wherein the inner face faces the body cold end of the elongate body; a channel having first and second hilt portions flanking a barrel portion, the channel extending entirely through the ring body from the outer face to the inner face, the hilt portions and the barrel portion dimensioned to permit the syringe hilt and the syringe barrel to pass respectively therethrough only while the syringe is in a first rotational orientation with respect to the ring body; first and second hilt recesses in the ring body flanking the barrel portion of the channel, the hilt recesses extending only partway through the ring body from the inner face towards the outer face and dimensioned to receive respective portions of the syringe hilt from the direction of the inner face of the ring body only while the syringe is in a second rotational orientation with respect to the ring body, the second rotational orientation being different than the first rotational orientation, wherein rotational movement of the syringe with respect to the locking ring is inhibited while the syringe hilt is received within the first and second hilt recesses; shelf structure associated with the hilt recesses for permitting rotation of the syringe between the first and second rotational orientations only while the syringe hilt received within the channel is longitudinally level with the inner face of the ring body; and resiliently deformable retention structure associated with the hilt recesses for selectively retaining the syringe hilt within the hilt recesses, the retention structure moveable between a rest position in which the hilt recesses are partially obstructed and a release position in which the hilt recesses are substantially unobstructed, said retention structure biased to said rest position.

In an embodiment, the resiliently deformable retention structure comprises a ridge projecting inwardly from a respective flexible outer wall of each of the first and second hilt recesses.

In an embodiment, each flexible outer wall is operable to move against the biasing between said rest position and said release position in response to application of a threshold level of force against the respective ridge by a respective portion of the syringe hilt, wherein: application of at least the threshold level of force by the syringe hilt against the respective ridge from the direction of the inner face of the locking ring causes the syringe hilt to be retained by the retention structure; and application of at least the threshold level of force by the syringe hilt against the respective ridge from the direction of the outer face of the locking ring causes the syringe hilt to be released by the retention structure.

In an embodiment, the shield further comprises a syringe adapter having a barrel adapter portion dimensioned to receive the syringe barrel and to, in turn, be received at least partly within the compartment of the elongate body; and a hilt adapter portion extending from the barrel adapter portion and dimensioned to receive the syringe hilt.

According to another aspect, there is provided a locking ring for a syringe shield, the syringe shield having: an elongate body comprising a compartment extending longitudinally therethrough from a body cold end to a body hot end, the compartment dimensioned to receive a syringe barrel of a syringe; a cold end cover dimensioned to at least enclose the compartment and the syringe at the body cold end; and a hot end cover dimensioned to at least enclose the compartment and the syringe at the body hot end, the locking ring dimensioned to be associated with the body cold end and to receive and engage a syringe hilt of the syringe to enable selective inhibition of one or both of: longitudinal and rotational movement of the syringe with respect to the body.

In an embodiment, the locking ring comprises a ring body having an outer face and an inner face, wherein the inner face faces the body cold end of the elongate body; a channel having first and second hilt portions flanking a barrel portion, the channel extending entirely through the ring body from the outer face to the inner face, the hilt portions and the barrel portion dimensioned to permit the syringe hilt and the syringe barrel to pass respectively therethrough only while the syringe is in a first rotational orientation with respect to the ring body; first and second hilt recesses in the ring body flanking the barrel portion of the channel, the hilt recesses extending only partway through the ring body from the inner face towards the outer face and dimensioned to receive respective portions of the syringe hilt from the direction of the inner face of the ring body only while the syringe is in a second rotational orientation with respect to the ring body, the second rotational orientation being different than the first rotational orientation, wherein rotational movement of the syringe with respect to the locking ring is inhibited while the syringe hilt is received within the first and second hilt recesses; shelf structure associated with the hilt recesses for permitting rotation of the syringe between the first and second rotational orientations only while the syringe hilt received within the channel is longitudinally level with the inner face of the ring body; and resiliently deformable retention structure associated with the hilt recesses for selectively retaining the syringe hilt within the hilt recesses, the retention structure moveable between a rest position in which the hilt recesses are partially obstructed and a release position in which the hilt recesses are substantially unobstructed, said retention structure biased to said rest position.

In an embodiment, the resiliently deformable retention structure comprises a ridge projecting inwardly from a respective flexible outer wall of each of the first and second hilt recesses.

In an embodiment, each flexible outer wall is operable to move against the biasing between said rest position and said release position in response to application of a threshold level of force against the respective ridge by a respective portion of the syringe hilt, wherein: application of at least the threshold level of force by the syringe hilt against the respective ridge from the direction of the inner face of the locking ring causes the syringe hilt to be retained by the retention structure; and application of at least the threshold level of force by the syringe hilt against the respective ridge from the direction of the outer face of the locking ring causes the syringe hilt to be released by the retention structure.

In accordance with another aspect, there is provided a unit dose shipment shield for containing a syringe comprising the locking ring.

In accordance with another aspect, there is provided a system for shipping radiopharmaceutical material comprising the shield, and a container in which the shield can be contained and that an operator can carry.

In an embodiment, the container is a shipping bag.

BRIEF DESCRIPTION OF THE DRAWINGS

In drawings that illustrate an embodiment of the invention by way of non-limiting example only.

DETAILED DESCRIPTION OF THE INVENTION

Figure 1:
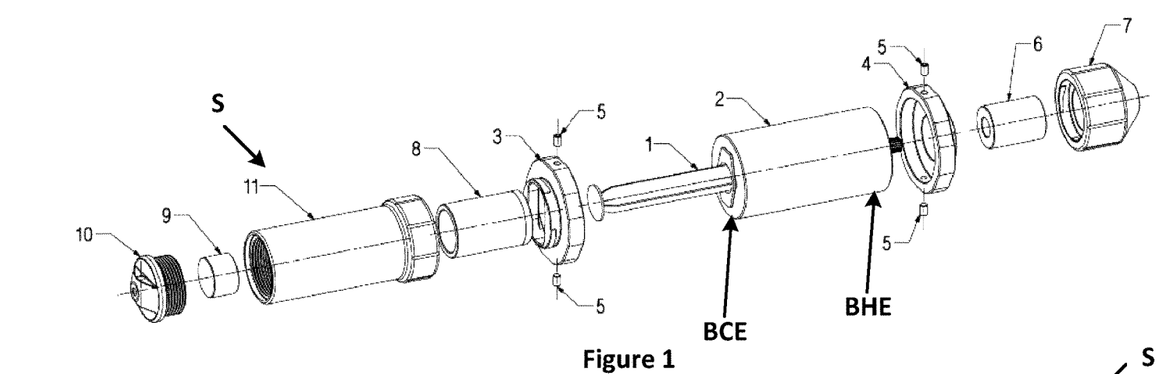
FIG. 1 is an exploded isometric view of a syringe shield and portions of a syringe to be contained within the syringe shield, according to an embodiment.

FIG. 1 is an exploded isometric view of a syringe shield S and portions of a syringe 1 to be contained within syringe shield S, according to an embodiment. In this embodiment, syringe shield S is suitable for containing and shipping a syringe that itself contains up to 1 Curie (Ci) of 131I-MIBG. As would be understood, 131I-MIBG is a combination of radioactive iodine and metaiodobenzylguanidine, suitable for diagnosis and localization of particular neuroendocrine tumors. Shield S can be used to contain other high energy radioisotopes for other applications, but in this embodiment is constructed with tungsten and anodized aluminum, and is sized and weighted to contain a syringe having a capacity of between 1cc and 60cc (cubic centimeters) in capacity, such as 1cc, 5cc, 60cc and other capacities. As would be understood, a 60cc capacity syringe, when filled such that its plunger is extended, can extend almost the length of a person's forearm. A given shield such as shield S is reusable, such that it can be used and re-used multiple times to contain and transport many different syringes, and to administer their contents as will be described, over time.

Shield S meets size and regulatory shielding requirements for shielding radiopharmaceutical contents during transportation, for example to comply with regulations in the United States governing the shipping of Yellow-II category radioactive packages and also to comply with United States OSHA (Occupational Safety and Health Administration) weight standards, in particular to weigh less than 50 lbs. An external package, as will be described, is configured to comply with IATA (International Air Transport Association) CFR/49 Class 7A regulations in order to be certified by United States Department of Transportation (DOT) for transport.

The modular design of shield S is adaptable to syringe size, volume of liquid (such as radiopharmaceutical liquid), isotope and activity level, and in embodiments can be sized or, as described, adapted, to accommodate materials and activity levels different from 131I-MIBG, such as emerging Theranostic agents that are in the mCi range, despite their energies being higher than 131I.

Figure 2:
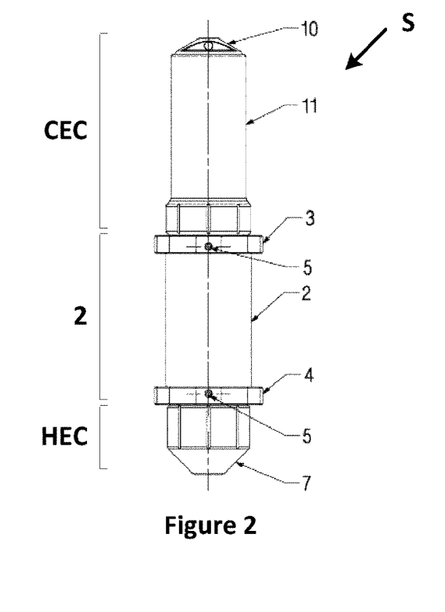
FIG. 2 is an elevation view of the syringe shield of FIG. 1, assembled and with hot and cold end covers interfacing with a shield body thereby to contain a syringe.
Figure 3:
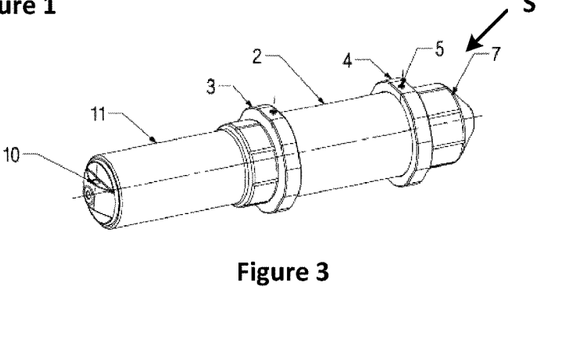
FIG. 3 is an isometric view of the syringe shield of FIG. 1, assembled and with hot and cold end covers interfacing with the shield body thereby to contain a syringe.

FIG. 2 is an elevation view of syringe shield S, assembled and with hot and cold end covers HEC, CEC each interfacing with a shield body 2 thereby to contain syringe 1. FIG. 3 is an isometric view of syringe shield S, assembled similarly as shown in FIG. 2. In this embodiment, elongate body 2 of shield S includes a compartment (C) extending longitudinally therethrough from a body cold end (BCE) to a body hot end (BHE). Compartment C is dimensioned to receive a syringe barrel of a syringe 1. Cold end cover CEC is dimensioned to receive and enclose a syringe plunger of syringe 1 that extends beyond the body cold end BCE. Cold end cover CEC is attachable at the body cold end BCE for enclosing compartment C and the syringe plunger at body cold end BCE thereby to shieldingly contain the biohazardous material in the syringe at body cold end BCE. Hot end cover HEC is attachable at body hot end BHE for at least enclosing compartment C at body hot end BHE thereby to shieldingly contain the biohazardous material in syringe 1 at body hot end BHE.

In this embodiment, elongate body 2 is cylindrical thereby to provide uniform thickness of tungsten about compartment C thereby to provide uniform shielding. Furthermore, the opening of compartment C has beveled edges to guide the syringe tip and then the syringe barrel an axial/longitudinal direction, thereby making it easier for a user to insert and center the syringe 1 within body 2.

In this embodiment, cold end cover CEC interfaces with elongate body 2 at its body cold end BCE via a first aluminium collar 3. Collar 3 has an inner portion attachable and, when shield S is assembled, attached to body cold end BCE of elongate body 2. In this embodiment, the inner portion of collar 3 is sized to receive body cold end BCE and set screws 5 are used to attach inner portion of collar 3 to body cold end BCE. An outer portion of collar 3 is reversibly attachable to cold end cover CEC. In particular, the outer portion of collar 3 comprises outwardly-projecting cams and cold end cover CEC comprises inwardly-projecting cams complementary to and engageable with the outwardly-projecting cams thereby to enable bayonet attachment of cold end cover CEC at body cold end BCE. As would be understood, a bayonet attachment permits a limited (for example, 60 degrees) rotation of cold end cover CEC with respect to the outer portion of collar 3 while the outer portion of collar 3 is being received within cold end cover CEC, thereby to cause the respective cams to engage one another to, in turn, connect cold end cover CEC, via collar 3, to elongate body 2. During such attachment, rotation in the opposite direction disengages the respective cams and enables cold end cover CEC to be detached from collar 3. It will be understood that, in alternative embodiments, other interface configurations, such as threads, can be integrated in order to provide for attachment and detachment of cold end cover CEC at the body cold end BCE of body 2.

In this embodiment, cold end cover CEC includes a shield cover 11, and a shield cover lid 10. Each of shield cover 11 and shield cover lid 10 is threaded such that shield cover lid 10 can be threaded into shield cover 11. A cylindrical void in shield cover lid 10 is dimensioned to receive a correspondingly-sized shielding puck 9 formed of tungsten that provides a radioactivity barrier at the distal end of cold end cover CEC intermediate cold end cover CEC and syringe 1. A shielding sleeve 8 formed of tungsten receives a part of the plunger of the syringe 1 so as to line the interior of the cold end cover CEC so as to be positioned intermediate the plunger and the shield cover 11.

In this embodiment, hot end cover HEC includes a shield cover lid 7 that interfaces with elongate body 2 at its body hot end BHE via a second aluminium collar 4. Collar 4 has an inner portion attachable and, when shield S is assembled, attached to body hot end BHE of elongate body 2. In this embodiment, the inner portion of collar 4 is sized to receive body hot end BHE and set screws 5 are used to attach the inner portion of collar 4 to body hot end BHE. An outer portion of collar 4 is reversibly attachable to hot end cover HEC. In particular, the outer portion of second collar 4 comprises outwardly-projecting cams and hot end cover HEC comprises inwardly-projecting cams complementary to and engageable with the outwardly-projecting cams thereby to enable bayonet attachment of hot end cover HEC at the body hot end BHE. Similar to cold end cover CEC, the bayonet attachment at the hot end permits a limited (for example, 60 degrees) rotation of hot end cover CEC with respect to the outer portion of collar 4 while the outer portion of collar 4 is being received within hot end cover HEC, thereby to cause the respective cams to engage one another to, in turn, connect hot end cover HEC, via collar 4, to elongate body 2. During such attachment, rotation in the opposite direction disengages the respective cams and enables hot end cover HEC to be detached from collar 4. It will be understood that, in alternative embodiments, other interface configurations, such as threads, can be integrated in order to provide for attachment and detachment of hot end cover HEC at the body hot end BHE of body 2. Hot end cover HEC has a planar exterior surface extending generally perpendicular to the axis of shield S, thereby to enable shield S to stand upright while distributing weight across the planar exterior surface.

A shielding puck 6 is received within hot end cover HEC to provide shielding intermediate hot end cover HEC and a syringe tip of syringe 1. In this embodiment, shielding puck 6 has an inlet, best seen in the cross-sectional depiction in FIG. 5 as providing a U-shaped cross-section to shielding puck 6, that is dimensioned as a crucible to at least partly receive the syringe tip while hot end cover HEC is attached at the body hot end BHE.

Figure 4:
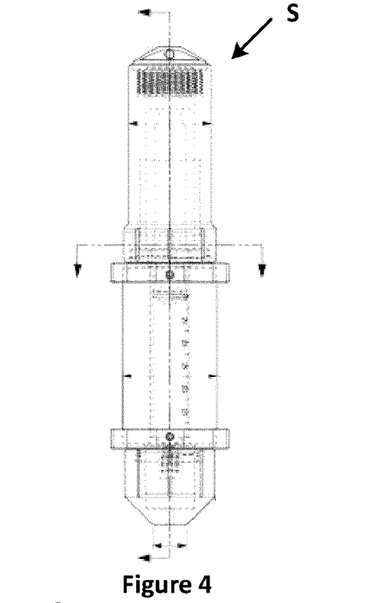
FIG. 4 is an elevation view of the syringe shield of FIG. 1, additionally showing relative positions and dimensions of inner compartments, components and a contained syringe.
Figure 5:
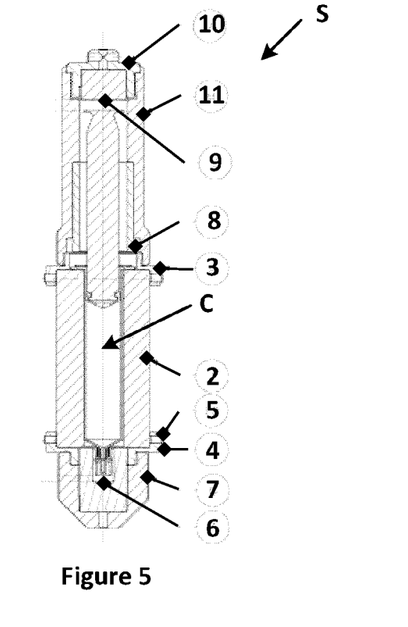
FIG. 5 is an elevational sectional view of the syringe shield of FIG. 1 and a contained syringe, as seen from the sectional line B-B in FIG. 4.
Figure 6:
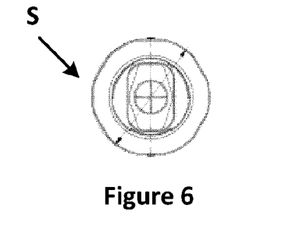
FIG. 6 is a top sectional view of a portion of the syringe shield of FIG. 1 and a contained syringe, as seen from the sectional line C-C in FIG. 4.
Figure 7:
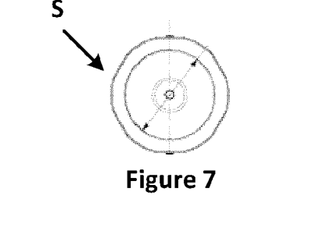
FIG. 7 is a bottom view of the syringe shield of FIG. 1.

FIG. 4 is an elevation view of syringe shield S, additionally showing relative positions and dimensions of inner compartments, components and contained syringe 1. FIG. 5 is an elevational sectional view of syringe shield S and contained syringe 1, as seen from the sectional line B-B in FIG. 4, additionally showing more clearly compartment C. FIG. 6 is a top sectional view of a portion of syringe shield S and contained syringe 1, as seen from the sectional line C-C in FIG. 4. FIG. 7 is a bottom view of syringe shield S.

In this embodiment, the outer diameters of collars 3 and 4 are not strictly cylindrical, but instead are comprised of a number of planar surfaces about their respective peripheries. The planar surfaces serve as the outermost diameters of shield S and are accordingly what shield S can rest upon when placed upon a supporting surface such as a table or lab bench. In this manner, shield S can more easily be kept in one place upon the supporting surface, rather than rolling across it. Alternative or additional structures for inhibiting rolling of shield S across a supporting surface may be provided.

Shield S, being modular, is capable of accommodating incorporation of additional Lucite layers, such as sleeves that can cooperate with sleeve 8 or compartment C, or pucks that can additionally be received where pucks 9 and 6 are received. The Lucite layers are useful for shielding for Beta radiation.

With shield S, removal of cold end cover CEC from collar 3 enables a syringe containing liquid material to be inserted tip first via collar 3 into compartment C of elongate body 2 until the syringe hilt contacts body cold end BCE. Depending on the size of syringe 1, its tip may at this point reach body hot end BHE of body 2 and be received within the inlet of puck 6 if hot end cover HEC is connected to body 2. Cold end cover CEC and hot end cover HEC may be independently connected or disconnected from body 2 depending on whether a syringe is being loaded or unloaded, is being contained for transportation or storage, or is being used to draw material out of syringe 1 while syringe 1 is being shielded by shield S. For example, a user may wish to load a syringe containing material into shield S by removing only cold end cover CEC while hot end cover HEC remains connected at body hot end BHE. In this way, with hot end cover HEC in place, there is shielding in place at the hot end of shield S. However, it may be useful and appropriate to load a syringe 1 into shield S with hot end cover HEC disconnected from body hot end BHE. Transportation of a contained syringe 1 will generally require that both cold end cover CEC and hot end cover HEC are connected to body 2. During administration of the contents of syringe 1, it may be useful to leave cold end cover CEC connected to body 2 while hot end cover HEC is removed, so that the tip of syringe 1 is available to be Luer-connected to a conduit for conveying the liquid downstream from syringe 1. Subsequent to this, it may be useful to remove cold end cover CEC thereby to enable a user or machine to depress the syringe plunger thereby to push the liquid out of the barrel of syringe 1 to continue downstream from syringe 1. Furthermore, a user may wish to remove the cold end cover CEC to remove a pre-loaded syringe from shield S, to perform processes such as radioactive assay with a dose calibrator, which is required prior to administering any dose to a patient. Once the administration is complete, cold end cover CEC and hot end cover HEC can each be reconnected thereby to shield syringe 1 while it is transported for disposal.

Figures 8, 9, 10:
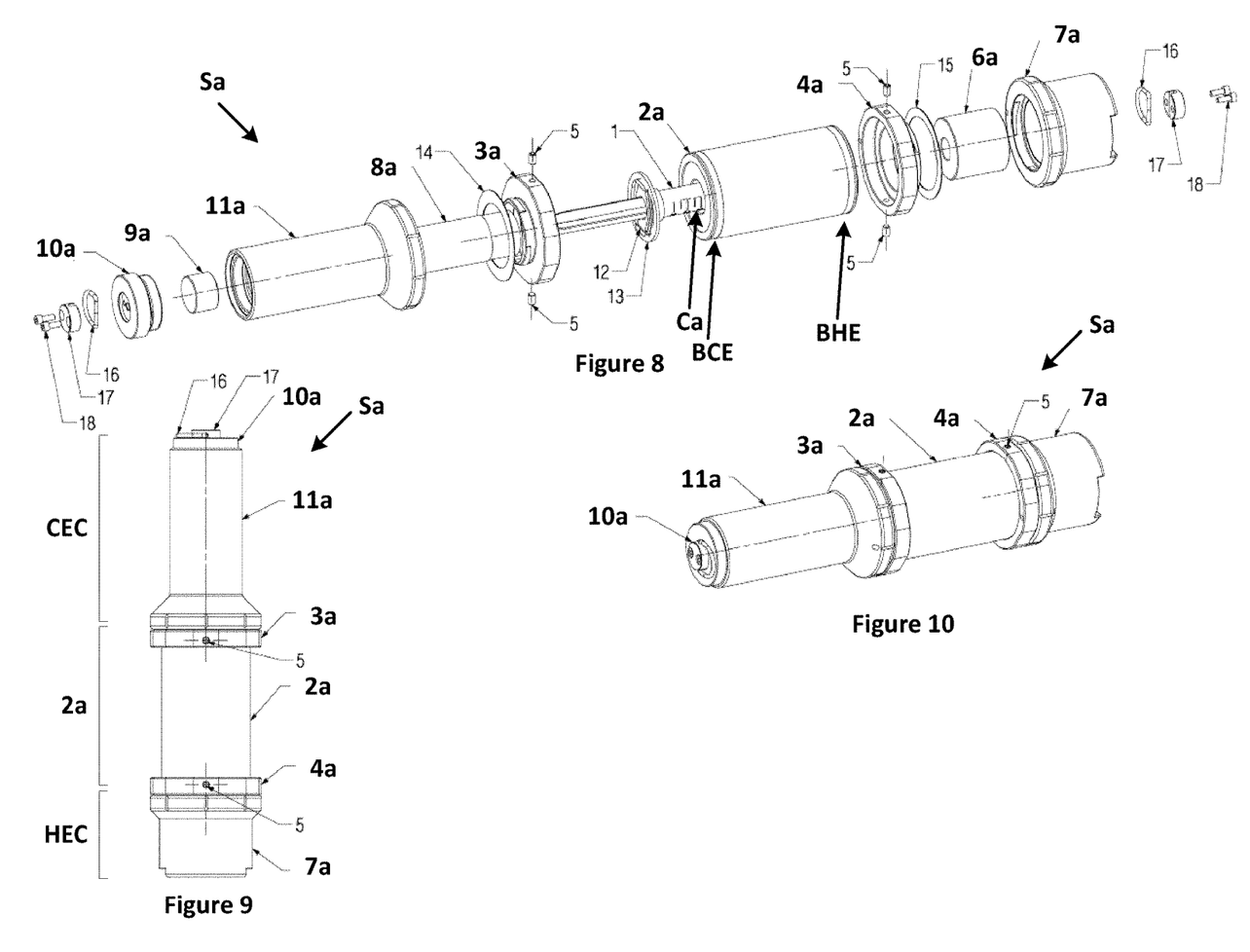
FIG. 8 is an exploded isometric view of a syringe shield and portions of a syringe to be contained within the syringe shield, according to an alternative embodiment.
FIG. 9 is an elevation view of the syringe shield of FIG. 8, assembled and with hot and cold end covers interfacing with a shield body thereby to contain a syringe.
FIG. 10 is an isometric view of the syringe shield of FIG. 8, assembled and with hot and cold end covers interfacing with the shield body thereby to contain a syringe.

FIG. 8 is an exploded isometric view of a syringe shield Sa and portions of a syringe 1 to be contained within a compartment Ca of syringe shield Sa, according to an alternative embodiment. Like syringe shield S, syringe shield Sa has cold and hot end covers CEC, HEC that are connectable at respective ends (body cold end BCE, body hot end BHE) of a shield body 2a. Similarly, in this embodiment, body 2a is cylindrical thereby to provide uniform thickness of tungsten about compartment Ca thereby to provide uniform shielding. Furthermore, the opening of compartment Ca has beveled edges to guide the syringe tip and then the syringe barrel an axial/longitudinal direction, thereby making it easier for a user to insert and center the syringe 1 within body 2a.

FIG. 9 is an elevation view of syringe shield Sa, assembled and with hot and cold end covers HEC, CEC interfacing with shield body 2a thereby to contain syringe 1. FIG. 10 is an isometric view of syringe shield Sa, assembled and with hot and cold end covers HEC, CEC interfacing with shield body 2a.

In this embodiment, cold end cover CEC interfaces with elongate body 2a at its body cold end BCE via a first aluminium collar 3a. Collar 3a has an inner portion attachable and, when shield Sa is assembled, attached to body cold end BCE of elongate body 2a. In this embodiment, the inner portion of collar 3a is sized to receive body cold end BCE and set screws 5 are used to attach inner portion of collar 3a to body cold end BCE. An outer portion of collar 3a is reversibly attachable to cold end cover CEC. In particular, the outer portion of collar 3a comprises outwardly-projecting cams and cold end cover CEC comprises inwardly-projecting cams complementary to and engageable with the outwardly-projecting cams thereby to enable bayonet attachment of cold end cover CEC at body cold end BCE. As described, a bayonet attachment permits a limited (for example, 60 degrees) rotation of cold end cover CEC with respect to the outer portion of collar 3a while the outer portion of collar 3a is being received within cold end cover CEC, thereby to cause the respective cams to engage one another to, in turn, connect cold end cover CEC, via collar 3a, to elongate body 2a. During such attachment, rotation in the opposite direction disengages the respective cams and enables cold end cover CEC to be detached from collar 3a. It will be understood that, in alternative embodiments, other interface configurations, such as threads, can be integrated in order to provide for attachment and detachment of cold end cover CEC at the body cold end BCE of body 2a.

In this embodiment, cold end cover CEC includes a shield cover 11a, and a shield cover lid 10a. Each of shield cover 11a and shield cover lid 10a is threaded such that shield cover lid 10a can be threaded into shield cover 11a. A cylindrical void in shield cover lid 10a is dimensioned to receive a correspondingly- sized shielding puck 9a formed of tungsten that provides a radioactivity barrier at the distal end of cold end cover CEC intermediate cold end cover CEC and syringe 1. A shielding sleeve 8a formed of tungsten receives a part of the plunger of the syringe 1 so as to line the interior of the cold end cover CEC so as to be positioned intermediate the plunger and the shield cover 11a. In this embodiment, shielding sleeve 8a includes two connected cylindrical tubes—the first tube having a substantially similar outer diameter as the inner diameter of shield cover 11a, so as to closely fit within shield cover 11a, and the second tube having substantially similar dimensions as the ovoid opening in collar 3a, so it can slide through this opening further towards the syringe hilt, reducing the distance that syringe 1 could move longitudinally towards the shield cover 11 a during transportation or other handling.

In this embodiment, hot end cover HEC includes a shield cover lid 7a that interfaces with elongate body 2a at its body hot end BHE via a second aluminium collar 4a. Collar 4a has an inner portion attachable and, when shield Sa is assembled, attached to body hot end BHE of elongate body 2a. In this embodiment, the inner portion of collar 4a is sized to receive body hot end BHE and set screws 5 are used to attach the inner portion of collar 4a to body hot end BHE. An outer portion of collar 4a is reversibly attachable to hot end cover HEC. In particular, the outer portion of second collar 4a comprises outwardly-projecting cams and hot end cover HEC comprises inwardly-projecting cams complementary to and engageable with the outwardly-projecting cams thereby to enable bayonet attachment of hot end cover HEC at the body hot end BHE. Similar to cold end cover CEC, the bayonet attachment at the hot end permits a limited (for example, 60 degrees) rotation of hot end cover CEC with respect to the outer portion of collar 4a while the outer portion of collar 4a is being received within hot end cover HEC, thereby to cause the respective cams to engage one another to, in turn, connect hot end cover HEC, via collar 4a, to elongate body 2a. During such attachment, rotation in the opposite direction disengages the respective cams and enables hot end cover HEC to be detached from collar 4a. It will be understood that, in alternative embodiments, other interface configurations, such as threads, can be integrated in order to provide for attachment and detachment of hot end cover HEC at the body hot end BHE of body 2a. Hot end cover HEC has a planar exterior surface extending generally perpendicular to the axis of shield Sa, thereby to enable shield Sa to stand upright while distributing weight across the planar exterior surface.

A shielding puck 6a is received within hot end cover HEC to provide shielding intermediate hot end cover HEC and a syringe tip of syringe 1. In this embodiment, shielding puck 6a has an inlet, like that shown for shield S as providing a U-shaped cross-section to shielding puck 6a, that is dimensioned as a crucible to at least partly receive the syringe tip while hot end cover HEC is attached at the body hot end BHE.

In this embodiment, the outer diameters of collars 3a and 4a are not strictly cylindrical, but instead are comprised of a number of planar surfaces about their respective peripheries. The planar surfaces serve as the outermost diameters of shield Sa and are accordingly what shield Sa can rest upon when placed upon a supporting surface such as a table or lab bench. In this manner, shield Sa can more easily be kept in one place upon the supporting surface, rather than rolling across it. Alternative or additional structures for inhibiting rolling of shield Sa across a supporting surface may be provided.

Shield Sa, being modular, is capable of accommodating incorporation of additional Lucite layers, such as sleeves that can cooperate with sleeve 8a or compartment Ca, or pucks that can additionally be received where pucks 9a and 6a are received. The Lucite layers are useful for shielding for Beta radiation.

In this embodiment a first gasket 14 is associated with the outer portion of collar 3a and is compressible between the cold end cover CEC and the outer portion of collar 3a during bayonet attachment thereby to inhibit unintentional detachment of cold end cover CEC from the outer portion of collar 3a. Furthermore, in this embodiment, a second gasket 15 is associated with the outer portion of collar 4a and compressible between the hot end cover HEC and the outer portion of collar 4a during bayonet attachment thereby to inhibit unintentional detachment of hot end cover HEC from the outer portion of collar 4a. First and second gaskets 14, 15 are formed from a material compatible with alcohols and other cleaning materials or may alternatively be replaced during cleaning prior to re-use with fresh gaskets.

Figures 11, 12:
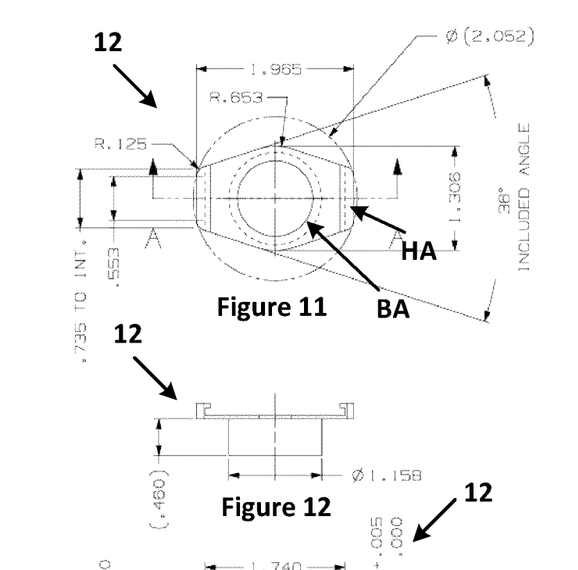
FIG. 11 is a top view of a syringe adapter for use with syringe shields, additionally showing relative positions and dimensions of barrel adapter and hilt adapter portions of the syringe adapter.
FIG. 12 is a front elevation view of the syringe adapter of FIG. 11.
Figure 13:
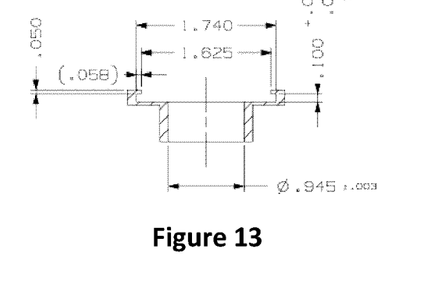
FIG. 13 is a front elevational sectional view of the syringe adapter of FIG. 11, as viewed from the line A-A in FIG. 11.
Figure 14:
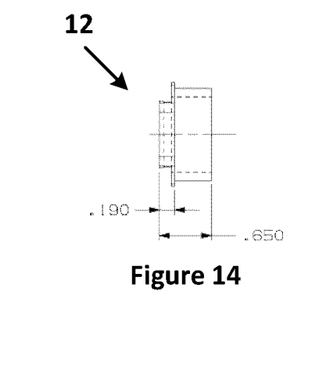
FIG. 14 is a right-side view of the syringe adapter of FIG. 11, additionally showing relative positions and dimensions of the barrel adapter and hilt adapter portions.
Figure 15:
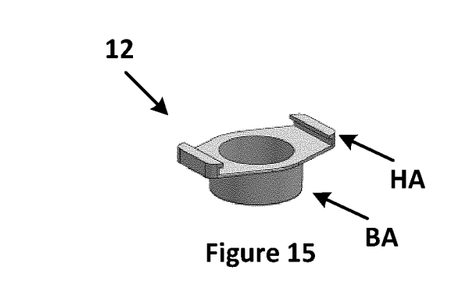
FIG. 15 is an isometric view of the syringe adapter of FIG. 11.

In this embodiment, a syringe adapter 12 is deployed within shield Sa to adapt for the dimensions of syringe 1 thereby to enable syringe 1 to be received within shield Sa comfortably but not too loosely. Syringe adapter 12 is used only for syringes that are very small as compared to compartment Ca and would be able to move laterally a significant amount as a result during transportation without syringe adapter 12. As would be understood, it is useful to keep a contained syringe from "rattling around" within syringe shield Sa or other syringe shields disclosed herein during transportation. FIG. 11 is a top view of syringe adapter 12, additionally showing relative positions and dimensions of barrel adapter portion BA and hilt adapter portion HA of syringe adapter 12. FIG. 12 is a front elevation view of syringe adapter 12. FIG. 13 is a front elevational sectional view of syringe adapter 12, as viewed from the line A-A in FIG. 11. Furthermore, FIG. 14 is a right-side view of syringe adapter 12, additionally showing relative positions and dimensions of the barrel adapter and hilt adapter portions, and FIG. 15 is an isometric view of syringe adapter 12. Barrel adapter portion BA is generally dimensioned to receive the syringe barrel and to, in turn, be received at least partly within the compartment of body 2a. Hilt adapter portion HA extends from the barrel adapter portion BA and is dimensioned to receive the syringe hilt.

In this embodiment a ring 16 is affixed to each of shield cover lid 10a and shield cover lid 7 via a respective clamp 17 held with screws 18 against a respective one of shield cover lid 10a and shield cover lid 7. Each ring 16 may be employed for holding shield Sa in a desired position during transportation or handling of shield Sa.

In this embodiment, syringe adapter 12 is, in turn, received within a locking ring 13 that is associated with body cold end BCE of body 2a. In embodiments, locking ring 13 is constructed from Delrin or HDPE (high density polyethylene). White Delrin can be preferable to provide flexibility. However, Delrin reacts to isopropyl alcohol, which is often used for sanitation in pharmacies. As such, other materials, or combinations of materials, may be employed where such materials are suitable for inclusion in the disclosed shipping system and permit functioning of the locking ring 13 as described below. The dimensions of the locking ring 12 are substantially identical to the recess inside of the shield collar at the cold end 3, wherein the locking ring 12 is received and connected.

Locking ring 13 is dimensioned to receive and engage a syringe hilt (or, as in this embodiment, the hilt adapter portion HA of syringe adapter 12) to enable selective inhibition of one or both of: longitudinal and rotational movement of the syringe 1 with respect to body 2a. Such inhibition is useful for easing connection or disconnection of a Luer-lock component to the syringe tip without a user having to grapple with the syringe moving longitudinally and/or rotationally to frustrate the connection or disconnection process. Such grappling might otherwise involve the user gripping the syringe plunger, which can unduly expose the user to the material contained within the syringe. Such inhibition is also useful for maintaining syringe 1 in a condition in which it does not "rattle around" either longitudinally or rotationally during transportation and other handling. In this embodiment, locking ring 13 is held against body cold end BCE of body 2a by collar 3a when collar 3a is attached to body cold end BCE of body 2a as described above.

In this embodiment, locking ring 13 is sized to permit passage therethrough of a syringe barrel (or, in this embodiment, the barrel adapter portion BA of syringe adapter 12) but to prevent passage therethrough of the syringe hilt (or, in this embodiment, the hilt adapter portion HA of syringe adapter 12). Locking ring 13 has an outer face and an inner face, where the inner face faces the body cold end BCE of the body 2a. At the outer face of locking ring 13 are slots into which the syringe hilt can be rotated and engaged within the slots in an interference fit (similarly to how the syringe hilt can be rotated with respect to the hilt adapter HA of syringe adapter 12 to be engaged within the hilt adapter HA). This enables the syringe hilt (or hilt adapter HA), once it has been slid longitudinally to contact the outer face of locking ring 13 at a first rotational orientation, to then be rotated into to a second rotational orientation to retain the syringe hilt (or hilt adapter HA) within the slots in the interference fit and accordingly inhibit the syringe 1 from unintended rotational or longitudinal movement.

While, in this embodiment, the slots of locking ring 13 are shown in FIG. 8 engaging the hilt adapter HA, it will be understood that the slots of locking ring 13 may engage a syringe hilt of a differently-sized syringe directly.

With shield Sa, removal of cold end cover CEC from collar 3a enables a syringe (with adapter 12, if used) containing liquid material to be inserted tip first via collar 3a and locking ring 13 into compartment Ca of elongate body 2a until the syringe hilt is in contact with to locking ring 13, which in turn is in contact with and held against body cold end BCE. Depending on the size of syringe 1, its tip may at this point reach body hot end BHE of body 2a and be received within the inlet of puck 6a if hot end cover HEC is connected to body 2a. Cold end cover CEC and hot end cover HEC may be independently connected or disconnected from body 2a depending on whether a syringe is being loaded or unloaded, is being contained for transportation or storage, or is being used to draw material out of syringe 1 while syringe 1 is being shielded by shield Sa. For example, a user may wish to load a syringe containing material into shield Sa by removing only cold end cover CEC while hot end cover HEC remains connected at body hot end BHE. In this way, with hot end cover HEC in place, there is shielding in place at the hot end of shield Sa. However, it may be useful and appropriate to load a syringe 1 into shield Sa with hot end cover HEC disconnected from body hot end BHE. Transportation of a contained syringe 1 will generally require that both cold end cover CEC and hot end cover HEC are connected to body 2a. During administration of the contents of syringe 1, it may be useful to leave cold end cover CEC connected to body 2a while hot end cover HEC is removed, so that the tip of syringe 1 is available to be Luer-connected to a conduit for conveying the liquid downstream from syringe 1. Subsequent to this, it may be useful to remove cold end cover CEC thereby to enable a user or machine to depress the syringe plunger thereby to push the liquid out of the barrel of syringe 1 to continue downstream from syringe 1. Furthermore, a user may wish to remove the cold end cover CEC to remove a pre-loaded syringe from shield Sa, to perform processes such as radioactive assay with a dose calibrator, which is required prior to administering any dose to a patient. Once the administration is complete, cold end cover CEC and hot end cover HEC can each be reconnected thereby to shield syringe 1 while it is transported for disposal.

Figure 16:
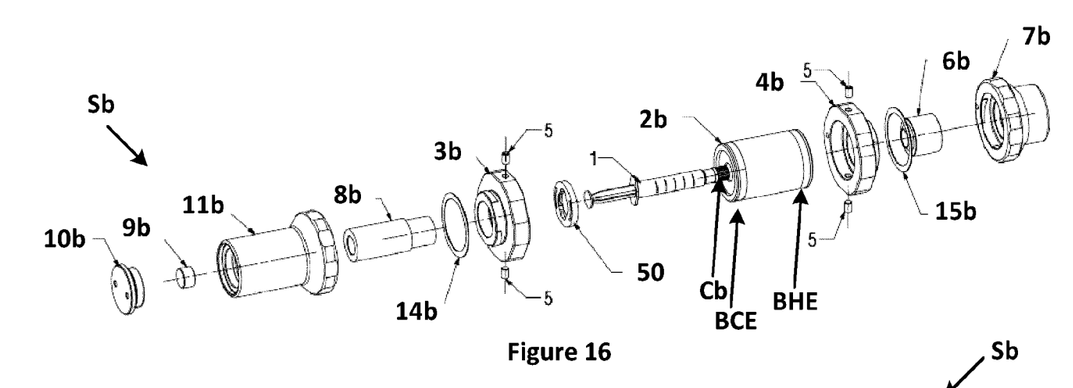
FIG. 16 is an exploded isometric view of a syringe and portions of a syringe to be contained within the syringe shield, according to another alternative embodiment.

FIG. 16 is an exploded isometric view of a syringe shield Sb and portions of a syringe 1 to be contained within a compartment Cb of syringe shield Sb, according to an alternative embodiment. Like syringe shields S and Sa, syringe shield Sb has cold and hot end covers CEC, HEC that are connectable at respective ends (body cold end BCE, body hot end BHE) of a shield body 2b. Similarly, in this embodiment, body 2b is cylindrical thereby to provide uniform thickness of tungsten about compartment Cb thereby to provide uniform shielding. Furthermore, the opening of compartment Cb has beveled edges to guide the syringe tip and then the syringe barrel an axial/longitudinal direction, thereby making it easier for a user to insert and center the syringe 1 within body 2a.

Figure 17:
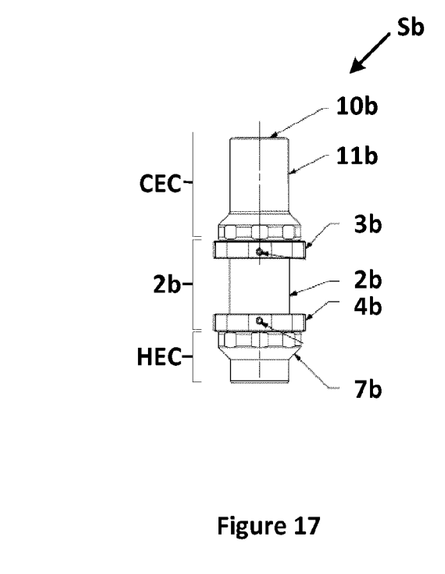
FIG. 17 is an elevation view of the syringe shield of FIG. 16, assembled and with hot and cold end covers interfacing with a shield body thereby to contain a syringe.
Figure 18:
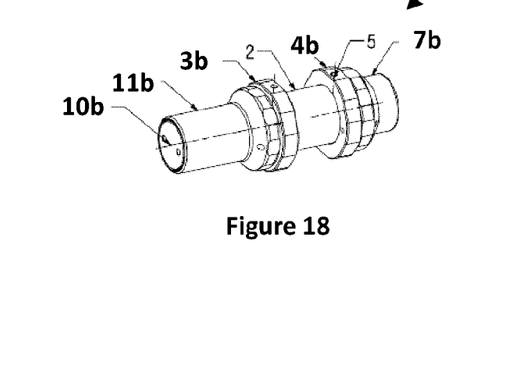
FIG. 18 is an isometric view of the syringe shield of FIG. 16, assembled and with hot and cold end covers interfacing with the shield body thereby to contain the syringe.

FIG. 17 is an elevation view of syringe shield Sb, assembled and with hot and cold end covers HEC, CEC interfacing with shield body 2b thereby to contain syringe 1. FIG. 18 is an isometric view of syringe shield Sb, assembled and with hot and cold end covers HEC, CEC interfacing with shield body 2b.

In this embodiment, cold end cover CEC interfaces with elongate body 2b at its body cold end BCE via a first aluminium collar 3b. Collar 3b has an inner portion attachable and, when shield Sb is assembled, attached to body cold end BCE of elongate body 2b. In this embodiment, the inner portion of collar 3b is sized to receive body cold end BCE and set screws 5 are used to attach inner portion of collar 3b to body cold end BCE. An outer portion of collar 3b is reversibly attachable to cold end cover CEC. In particular, the outer portion of collar 3b comprises outwardly-projecting cams and cold end cover CEC comprises inwardly-projecting cams complementary to and engageable with the outwardly-projecting cams thereby to enable bayonet attachment of cold end cover CEC at body cold end BCE. As described, a bayonet attachment permits a limited (for example, 60 degrees) rotation of cold end cover CEC with respect to the outer portion of collar 3b while the outer portion of collar 3b is being received within cold end cover CEC, thereby to cause the respective cams to engage one another to, in turn, connect cold end cover CEC, via collar 3b, to elongate body 2b. During such attachment, rotation in the opposite direction disengages the respective cams and enables cold end cover CEC to be detached from collar 3*b*. It will be understood that, in alternative embodiments, other interface configurations, such as threads, can be integrated in order to provide for attachment and detachment of cold end cover CEC at the body cold end BCE of body 2*b*.

In this embodiment, cold end cover CEC includes a shield cover 11*b*, and a shield cover lid 10*b*. Each of shield cover 11*b* and shield cover lid 10*b* is threaded such that shield cover lid 10*b* can be threaded into shield cover 11*b*. A cylindrical void in shield cover lid 10*b* is dimensioned to receive a correspondingly-sized shielding puck 9*b* formed of tungsten that provides a radioactivity barrier at the distal end of cold end cover CEC intermediate cold end cover CEC and syringe 1. A shielding sleeve 8*b* formed of tungsten receives a part of the plunger of the syringe 1 so as to line the interior of the cold end cover CEC so as to be positioned intermediate the plunger and the shield cover 11*b*.

In this embodiment, hot end cover HEC includes a shield cover lid 7*b* that interfaces with elongate body 2*b* at its body hot end BHE via a second aluminium collar 4*b*. Collar 4*b* has an inner portion attachable and, when shield Sb is assembled, attached to body hot end BHE of elongate body 2*b*. In this embodiment, the inner portion of collar 4*b* is sized to receive body hot end BHE and set screws 5 are used to attach the inner portion of collar 4*b* to body hot end BHE. An outer portion of collar 4*b* is reversibly attachable to hot end cover HEC. In particular, the outer portion of second collar 4*b* comprises outwardly-projecting cams and hot end cover HEC comprises inwardly-projecting cams complementary to and engageable with the outwardly-projecting cams thereby to enable bayonet attachment of hot end cover HEC at the body hot end BHE. Similar to cold end cover CEC, the bayonet attachment at the hot end permits a limited (for example, 60 degrees) rotation of hot end cover CEC with respect to the outer portion of collar 4*b* while the outer portion of collar 4*b* is being received within hot end cover HEC, thereby to cause the respective cams to engage one another to, in turn, connect hot end cover HEC, via collar 4*b*, to elongate body 2*b*. During such attachment, rotation in the opposite direction disengages the respective cams and enables hot end cover HEC to be detached from collar 4*b*. It will be understood that, in alternative embodiments, other interface configurations, such as threads, can be integrated in order to provide for attachment and detachment of hot end cover HEC at the body hot end BHE of body 2*b*. Hot end cover HEC has a planar exterior surface extending generally perpendicular to the axis of shield Sb, thereby to enable shield Sb to stand upright while distributing weight across the planar exterior surface.

A shielding puck 6*b* is received within hot end cover HEC to provide shielding intermediate hot end cover HEC and a syringe tip of syringe 1. In this embodiment, shielding puck 6*b* has an inlet, like that shown for shield S as providing a U-shaped cross-section to shielding puck 6*b*, that is dimensioned as a crucible to at least partly receive the syringe tip while hot end cover HEC is attached at the body hot end BHE.

In this embodiment, the outer diameters of collars 3*b* and 4*b* are not strictly cylindrical, but instead are comprised of a number of planar surfaces about their respective peripheries. The planar surfaces serve as the outermost diameters of shield Sb and are accordingly what shield Sb can rest upon when placed upon a supporting surface such as a table or lab bench. In this manner, shield Sb can more easily be kept in one place upon the supporting surface, rather than rolling across it. Alternative or additional structures for inhibiting rolling of shield Sb across a supporting surface may be provided.

Shield Sb, being modular, is capable of accommodating incorporation of additional Lucite layers, such as sleeves that can cooperate with sleeve 8*b* or compartment Cb, or pucks that can additionally be received where pucks 9*b* and 6*b* are received. The Lucite layers are useful for shielding for Beta radiation.

In this embodiment a first gasket 14*b* is associated with the outer portion of collar 3*b* and is compressible between the cold end cover CEC and the outer portion of collar 3*b* during bayonet attachment thereby to inhibit unintentional detachment of cold end cover CEC from the outer portion of collar 3*b*. Furthermore, in this embodiment, a second gasket 15*b* is associated with the outer portion of collar 4*b* and compressible between the hot end cover HEC and the outer portion of collar 4*b* during bayonet attachment thereby to inhibit unintentional detachment of hot end cover HEC from the outer portion of collar 4*b*. First and second gaskets 14*b*, 15*b* are formed from a material compatible with alcohols and other cleaning materials or may alternatively be replaced during cleaning prior to re-use with fresh gaskets.

In this embodiment, the syringe hilt is received within an alternative locking ring 50 that is associated with body cold end BCE of body 2*b*. In embodiments, locking ring 50 is constructed from Delrin or HDPE (high density polyethylene). White Delrin can be preferable to provide flexibility. However, Delrin reacts to isopropyl alcohol, which is often used for sanitation in pharmacies. As such, other materials, or combinations of materials, may be employed where such materials are suitable for inclusion in the disclosed shipping system and permit functioning of the locking ring 50 as described below.

Figure 19:
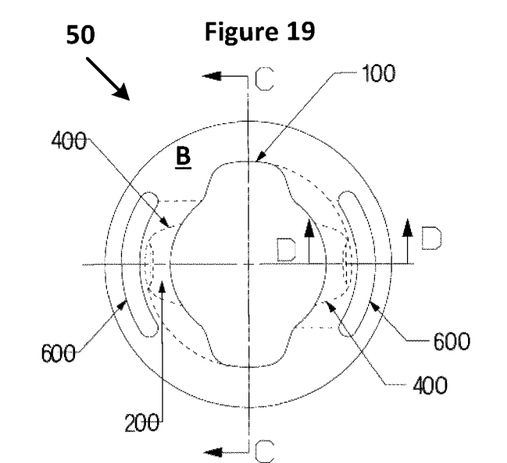
FIG. 19 is a top view of a locking ring for a syringe shield, additionally showing relative positions of components of the locking ring.
Figure 20:
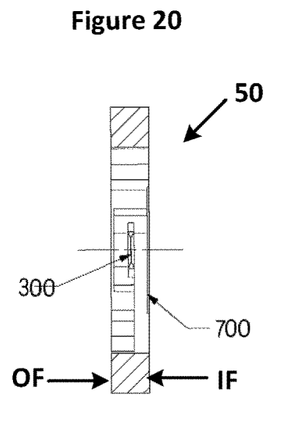
FIG. 20 is a sectional right-side view of the locking ring of FIG. 19, as view from the line C-C in FIG. 19.
Figure 21:
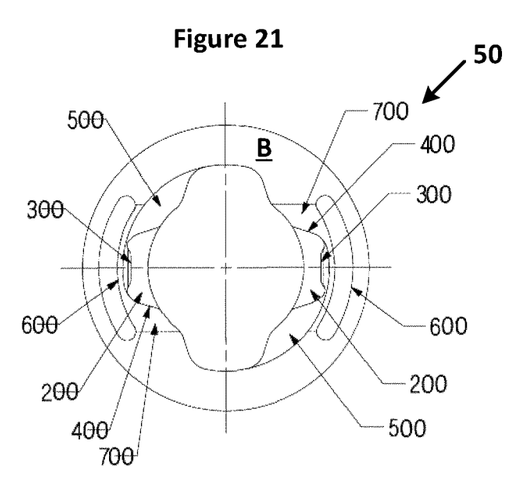
FIG. 21 is a bottom view of the locking ring of FIG. 19.
Figures 22, 23:
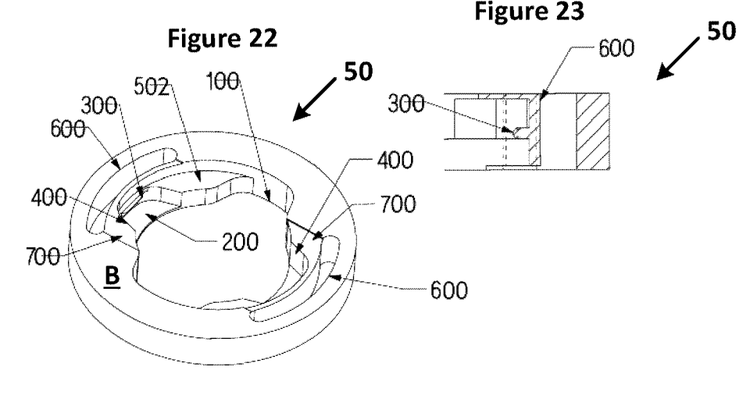
FIG. 22 is an isometric bottom view of the locking ring of FIG. 19.
FIG. 23 is a sectional front-side view of a portion of the locking ring of FIG. 19, as viewed from the line D-D in FIG. 19.

Locking ring 50 is dimensioned to receive and engage the syringe hilt to enable selective inhibition of one or both of: longitudinal and rotational movement of the syringe 1 with respect to body 2*b*. Such inhibition is useful for easing connection or disconnection of a Luer-lock component to the syringe tip without a user having to grapple with the syringe moving longitudinally and/or rotationally to frustrate the connection or disconnection process. Such grappling might otherwise involve the user gripping the syringe plunger, which can unduly expose the user to the material contained within the syringe. Such inhibition is also useful for maintaining syringe 1 in a condition in which it does not "rattle around" either longitudinally or rotationally during transportation and other handling. In this embodiment, locking ring 50 is held against body cold end BCE of body 2*b* by collar 3*b* when collar 3*b* is attached to body cold end BCE of body 2*b* as described above. FIG. 19 is a top view of locking ring 50, additionally showing (in dashed lines) relative positions of components of the locking ring not actually visible when locking ring 50 is viewed from the top. FIG. 20 is a sectional right-side view of locking ring 50, as viewed from the line C-C in FIG. 19. FIG. 21 is a bottom view of locking ring 50. FIG. 22 is an isometric bottom view of locking ring 50. FIG. 23 is a sectional front-side view of a portion of locking ring 50, as viewed from the line D-D in FIG. 19.

In this embodiment, locking ring 50 includes a ring body B having an outer face OF and an inner face IF. Inner face IF faces the body cold end BCE of elongate body 2*b*. A channel 100 has first and second hilt portions flanking a barrel portion and extends entirely through ring body B from outer face OF to inner face IF. The hilt portions and the barrel portion are sized and shaped to permit the syringe hilt and the syringe barrel of a syringe 1 to pass respectively therethrough only while the syringe 1 is in a first rotational orientation with respect to ring body B. This first rotational orientation is shown in FIGS. 19 and 21, with the barrel portion being central to locking ring 50 and the hilt portions flanking the barrel portion such that a first hilt portion is 0 degrees (i.e., twelve o'clock) and a second hilt portion is at 180 degrees (i.e., six o'clock).

First and second hilt recesses 200 in the ring body flank the barrel portion of the channel 100 at 90 degrees (i.e., three o'clock) and 270 degrees (i.e., nine o'clock). In this embodiment, hilt recesses 200 extend only partway through the ring body B from inner face IF towards outer face OF. More particularly, hilt recesses 200 are accessible to syringe hilt from inner face IF, but not from outer face OF. Hilt recesses 200 are sized, shaped and positioned to receive respective portions of the syringe hilt from the direction of inner face IF of ring body B only while the syringe is in a particular second rotational orientation with respect to the ring body B that is different from the first rotational orientation. In this embodiment, if the first rotational orientation is 0 degrees, the second rotational orientation is 90 degrees (as can be seen from FIG. 19, in particular).

Rotational movement of syringe 1 with respect to locking ring 50 is inhibited while the syringe hilt is received within the first and second hilt recesses 200. In this embodiment, the inhibition of rotation is provided by shelf structure, in particular shelves 500. Shelves 500 do not extend all the way to inner face IF thereby to inhibit rotation of a syringe by inhibiting rotation of the syringe hilt between the first rotational orientation and the second rotational orientation only until the syringe hilt is longitudinally level with inner face IF. Put another way, shelves 500 extend only so far as to permit rotation of the syringe between the first and second rotational orientations only while the syringe hilt received within channel 100 is longitudinally level with the inner face IF.

Resiliently deformable retention structure is associated with hilt recesses 200 for selectively retaining the syringe hilt within hilt recesses 200. The retention structure is moveable between a rest position in which hilt recesses 200 are partially obstructed and a release position in which hilt recesses 200 are substantially unobstructed. The retention structure is biased to the rest position. In this embodiment, the resiliently deformable retention structure comprises a ridge 300 projecting inwardly from a respective flexible outer wall 400 of each of the first and second hilt recesses 200. Each flexible outer wall 400 is provided by holes 600 in body B behind outer wall 400 thereby providing a respective area into which a respective outer wall 400 may flex to. Each flexible outer wall 400 is operable to move against the biasing between the rest position and the release position in response to application of a threshold level of force against the respective ridge 300 by a respective portion of the syringe hilt.

Application of at least the threshold level of force by the syringe hilt against the respective ridge 300 from the direction of the inner face IF causes the syringe hilt to push the ridge 300 out of the way thereby to cause the syringe hilt to move past the ridge 300. Once past, the ridge snaps back under the bias with a "click" as the respective flexible outer wall 400 snaps back against the syringe hilt such that the ridge 300 overlaps the syringe hilt slightly thereby to retain the syringe hilt between the ridge 300 and the bottom of the hilt recess 200. Similarly, application of at least the threshold level of force by the syringe hilt against the respective ridge 300 from the direction of the outer face OF causes the syringe hilt to push the ridge 300 out of the way thereby to cause the syringe hilt to move past the ridge 300 so the hilt can be removed from the hilt recess 200. Once past, the ridge snaps back under the bias with another "click" as the respective flexible outer wall 400 snaps back against the syringe hilt such that the ridge 300 "underlaps" the syringe hilt slightly thereby to retain the syringe hilt. Furthermore, as the syringe hilt is snapped out of the hilt recess 200, typically by pushing the syringe plunger as far as it will go into the syringe barrel thus urging the syringe hilt to move longitudinally towards the body cold end BCE, the syringe hilt will "hit" against the body cold end BCE creating somewhat of a "click" sound. Once this is done the syringe hilt, being longitudinally level again with the inner face IF, may again be rotated towards the first rotational orientation if desired.

Locking ring 50 may be employed in embodiments of syringe shield S and Sa, or other embodiments, and may be usefully made available as a standalone product that can be purchased as a replacement for a previously-used and potentially contaminated locking ring of the same or similar type.

With shield Sb, removal of cold end cover CEC from collar 3*b* enables a syringe containing liquid material to be inserted tip first via collar 3*b* and locking ring 50 into compartment Cb of elongate body 2*b* while the syringe hilt is in a first rotational orientation until the syringe hilt is in contact with body cold end BCE of body 2*b*. Depending on the size of syringe 1, its tip may at this point reach body hot end BHE of body 2*b* and be received within the inlet of puck 6*b* if hot end cover HEC is connected to body 2*b*. Furthermore, as described above, syringe 1 may at this longitudinal position be rotated past the shelf structure to the second rotational orientation, and then longitudinally pulled so as to recede slightly from the body cold end BCE thereby to engage and then be retained by the retention structure.

Cold end cover CEC and hot end cover HEC may be independently connected or disconnected from body 2*b* depending on whether a syringe is being loaded or unloaded, is being contained for transportation or storage, or is being used to draw material out of syringe 1 while syringe 1 is being shielded by shield Sb. For example, a user may wish to load a syringe containing material into shield by removing only cold end cover CEC while hot end cover HEC remains connected at body hot end BHE. In this way, with hot end cover HEC in place, there is shielding in place at the hot end of shield Sb. However, it may be useful and appropriate to load a syringe 1 into shield Sb with hot end cover HEC disconnected from body hot end BHE. Transportation of a contained syringe 1 will generally require that both cold end cover CEC and hot end cover HEC are connected to body 2*b*. During administration of the contents of syringe 1, it may be useful to leave cold end cover CEC connected to body 2*b* while hot end cover HEC is removed, so that the tip of syringe 1 is available to be Luer-connected to a conduit for conveying the liquid downstream from syringe 1. Subsequent to this, it may be useful to remove cold end cover CEC thereby to enable a user or machine to depress the syringe plunger thereby to push the liquid out of the barrel of syringe 1 to continue downstream from syringe 1. Furthermore, a user may wish to remove the cold end cover CEC to remove a pre-loaded syringe from shield Sb, to perform processes such as radioactive assay with a dose calibrator, which is required prior to administering any dose to a patient. Once the administration is complete, cold end cover CEC and hot end cover HEC can each be reconnected thereby to shield syringe 1 while it is transported for disposal.

In embodiments disclosed herein, thicknesses of hot/cold end covers as well as those of the tungsten pucks are all optimized based upon source shape (in this case syringe size e.g. 1-60 cc's), source volume and type of radioactive emission (Beta, Gamma, Positron or mixed).

Figure 24A:
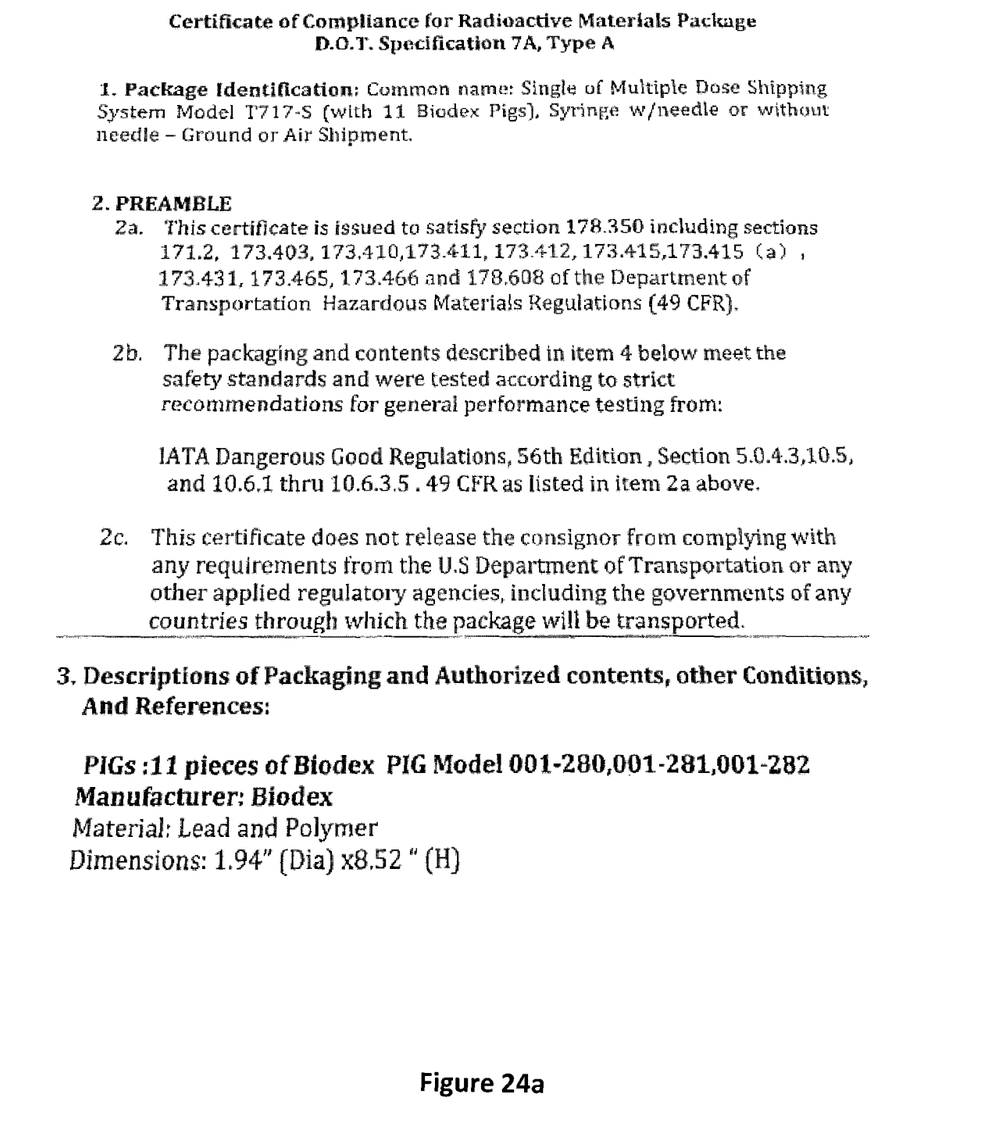
FIGS. 24a and 24b, hereinafter referred to simply as FIG. 24, is an example certificate of compliance for a shipping system bag.
Figure 24B:
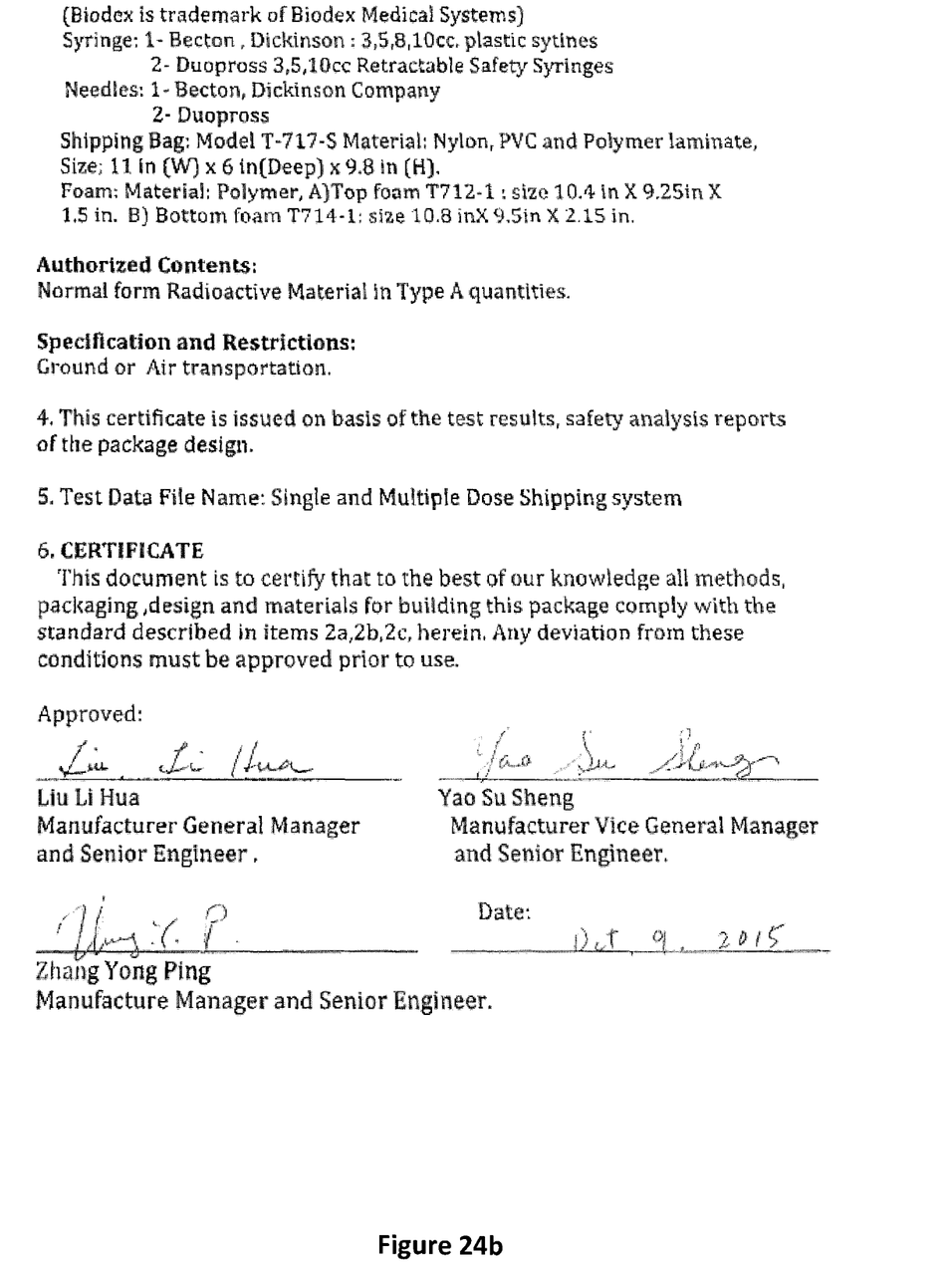

Another aspect of an overall shipping system in addition to the above-described shield, is an external container, preferably in the form of a shipping package or bag. There is known, and commonly used, a prior art shipping bag, known as a Type A IATA CFR49 compliant shipping bag. An example of such a bag may be seen at:

http://www.biodex.com/nuclear-medicine/products/radiopharmacy/pro-tec-pig-and-accessories/pro-tec-pig-shipping-bag An example certificate of compliance for the bag is provided herein in FIG. 24, which also includes references to various regulations pertaining to the bag and its suitability for use. This type of bag is an example of a package known to be used in Nuclear Medicine, particularly for the SPECT industry, which relies upon Tc99m radiopharmaceuticals. Tc99m is a low energy isotope. However, there are no known or viable (i.e., compliant with regulations) shipping options for high energy isotopes currently, to the knowledge of the applicant. Such high energy isotopes include, for examples, Ga68, Lu177, Zr89, Sr89 and Cu64 based isotopes. The modularity of the above-described shield design and the optimization of a "universal" package size enables shipping of these emerging high energy isotopes the same way Tc99m is currently shipped. Specifically, the universal package when combined with the above-described modular shield will allow shipments to be treated and approved as Yellow-II category radioactive packages.

Embodiments of the shield in accordance with the invention may be combined as a system with an external package that complies with, inter alia, 49 CFR §§ 172.403 Class 7, 173.411-173.413, and 10 CFR § 71.

A universal package may be produced based on the principles herein, with particular utility for shipping I-131, Ga-68, Zr-89 and Cu-64 isotopes. More particularly, while the I-131, Ga-68, Zr-89 and Cu-64 applications are particular to certain syringe sizes and radiopharmaceutical volume and activity, the principles described herein are more universally applicable, particularly for emerging Theranostic agents that are in the mCi range, despite their energies being higher than I-131.

This type of bag is an example of a package known to be used in Nuclear Medicine, particularly for the SPECT industry, which relies upon Tc99m radiopharmaceuticals. Tc99m is a low energy isotope. However, to the knowledge of the applicant, there are no known or viable shipping options for high energy isotopes. Such high energy isotopes include, for example, Ga-68, Lu-177, Zr-89, Sr-89 and Cu-64 based isotopes. The modularity of the above-described shield design and the optimization of a "universal" package size enables shipping of these emerging high energy isotopes the same way Tc99m is currently shipped.

In a preferred embodiment of the shipping system, an operator places the shield into the shipping bag in a generally vertical orientation, inserting the hot end of the shield into an appropriately-sized recess in a foam liner at the bottom of the bag. The operator then places a separate foam block on top of the shield to fill any space between the distal cold end of the shield and the opening of the bag, which closely invests around shield.

In this embodiment, the shield is suspended vertically within the Y plane, so that syringe is roughly centred within the three axes.

In another preferred embodiment, an operator places the shield into the shipping bag in a generally horizontal orientation, inserting the shield into an appropriately-sized recess in the foam liner at the bottom of the bag. The operator then places a separate foam block on top of the shield to fill any space between the upward-facing side of the shield and the opening of the bag, which closely invests around shield.

In an embodiment, the bag is scaled appropriately to work in conjunction with shielding elements to yield Yellow-II hazard rating with up to 1 Ci for I-131, up to 16.5mCi for Ga-68, and up to 12mCi for Cu-64. In other embodiments, the bag may be scaled to accommodate shielding elements to accommodate other ratings based on other isotopes.

Alternatives are possible.

What is claimed is:

1. A shield for a syringe, the shield comprising:
   an elongate body comprising a compartment extending longitudinally therethrough from a body cold end to a body hot end, the compartment dimensioned to receive a barrel of a syringe;
   a cold end cover dimensioned to receive and enclose a plunger of the syringe extending beyond the body cold end, the cold end cover selectively attachable at the body cold end for enclosing the compartment and the plunger at the body cold end thereby to shieldingly contain the syringe at the body cold end;
   a hot end cover selectively attachable at the body hot end for at least enclosing the compartment at the body hot end thereby to shieldingly contain the syringe at the body hot end; and
   a locking ring associated with the compartment, the locking ring dimensioned to receive and engage a hilt of the syringe to enable selective inhibition of one or both of: longitudinal and rotational movement of the syringe with respect to the body.

2. The shield of claim 1, wherein the elongate body is cylindrical.

3. The shield of claim 1, comprising:
   a first collar comprising an inner portion attached to the body cold end and an outer portion attachable to the cold end cover.

4. The shield of claim 3, wherein the outer portion of the first collar comprises outwardly-projecting cams and the cold end cover comprises inwardly-projecting cams complementary to and engageable with the outwardly-projecting cams of the outer portion of the first collar thereby to enable bayonet attachment of the cold end cover at the body cold end.

5. The shield of claim 4, further comprising:
   a first gasket associated with the outer portion of the first collar and compressible between the cold end cover and the outer portion of the first collar during bayonet attachment thereby to inhibit unintentional detachment of the cold end cover from the outer portion.

6. The shield of claim 5, comprising:
   a second collar comprising an inner portion attached to the body hot end and an outer portion attachable to the hot end cover.

7. The shield of claim 6, wherein the outer portion of the second collar comprises outwardly-projecting cams and the hot end cover comprises inwardly-projecting cams complementary to and engageable with the outwardly-projecting cams of the outer portion of the second collar thereby to enable bayonet attachment of the hot end cover at the body hot end.

8. The shield of claim 7, further comprising:
a second gasket associated with the outer portion of the second collar and compressible between the hot end cover and the outer portion of the second collar during bayonet attachment thereby to inhibit unintentional detachment of the hot end cover from the outer portion.

9. The shield of claim 1, further comprising:
a shielding sleeve lining an interior of the cold end cover to be intermediate the cold end cover and the plunger; and
a shielding puck at a distal end of the cold end cover to be intermediate the cold end cover and the plunger.

10. The shield of claim 9, wherein the cold end cover comprises a removable lid at the distal end of the cold end cover, the lid dimensioned to receive the shielding puck.

11. The shield of claim 1, further comprising:
a shielding puck at a distal end of the hot end cover to be intermediate the hot end cover and a tip of the syringe.

12. The shield of claim 11, wherein the shielding puck at the distal end of the hot end cover comprises an inlet dimensioned to at least partly receive the tip while the hot end cover is attached at the body hot end.

13. The shield of claim 1, wherein the locking ring comprises:
a ring body having an outer face and an inner face, wherein the inner face faces the body cold end of the elongate body;
a channel having first and second hilt portions flanking a barrel portion, the channel extending entirely through the ring body from the outer face to the inner face, the hilt portions and the barrel portion dimensioned to permit the hilt and the barrel to pass respectively therethrough only while the syringe is in a first rotational orientation with respect to the ring body;
first and second hilt recesses in the ring body flanking the barrel portion of the channel, the hilt recesses extending only partway through the ring body from the inner face towards the outer face and dimensioned to receive respective portions of the hilt from the direction of the inner face of the ring body only while the syringe is in a second rotational orientation with respect to the ring body, the second rotational orientation being different than the first rotational orientation, wherein rotational movement of the syringe with respect to the locking ring is inhibited while the hilt is received within the first and second hilt recesses;
shelf structure associated with the hilt recesses for permitting rotation of the syringe between the first and second rotational orientations only while the hilt received within the channel is longitudinally level with the inner face of the ring body; and
resiliently deformable retention structure associated with the hilt recesses for selectively retaining the hilt within the hilt recesses, the retention structure moveable between a rest position in which the hilt recesses are partially obstructed and a release position in which the hilt recesses are substantially unobstructed, said retention structure biased to said rest position.

14. The shield of claim 13, wherein the resiliently deformable retention structure comprises a ridge projecting inwardly from a respective flexible outer wall of each of the first and second hilt recesses.

15. The shield of claim 14, wherein each flexible outer wall is operable to move against the biasing between said rest position and said release position in response to application of a threshold level of force against the respective ridge by a respective portion of the hilt, wherein:
application of at least the threshold level of force by the hilt against the respective ridge from the direction of the inner face of the locking ring causes the hilt to be retained by the retention structure; and
application of at least the threshold level of force by the hilt against the respective ridge from the direction of the outer face of the locking ring causes the hilt to be released by the retention structure.

16. The shield of claim 1, further comprising a syringe adapter having:
a barrel adapter portion dimensioned to receive the barrel and to, in turn, be received at least partly within the compartment of the elongate body; and
a hilt adapter portion extending from the barrel adapter portion and dimensioned to receive the hilt.

17. A system for shipping radiopharmaceutical material comprising:
the shield of claim 1; and
a container in which the shield can be contained and that an operator can carry.

18. The system of claim 17, wherein the container is a shipping bag.

* * * * *